United States Patent [19]
Taylor et al.

[11] Patent Number: 5,879,679
[45] Date of Patent: Mar. 9, 1999

[54] ANTIGEN-BASED HETEROPOLYMERS AND METHOD FOR TREATING AUTOIMMUNE DISEASES USING THE SAME

[75] Inventors: Ronald P. Taylor; Polly J. Ferguson; Edward N. Martin, Jr., all of Charlottesville, Va.; William M. Sutherland, Earlysville, Va.; Craig J. Reist, Hillsborough, N.C.; Kirsten Greene, Baltimore, Md.; Cyd Johnson, San Francisco, Calif.

[73] Assignee: University of Virginia Alumni Patents Foundation, Charlottesville, Va.

[21] Appl. No.: 460,861

[22] Filed: Jun. 5, 1995

Related U.S. Application Data

[62] Division of Ser. No. 202,572, Feb. 28, 1994.

[51] Int. Cl.$^6$ .......................... A61K 39/395; C07K 16/00
[52] U.S. Cl. ..................... 424/178.1; 424/153.1; 530/388.3; 530/389.6; 530/391.1; 530/391.7
[58] Field of Search .............................. 424/153.1, 178.1; 530/388.3, 389.6, 391.1, 391.7

[56] References Cited

PUBLICATIONS

Liszewski et al., The Complement System, Fundamental Immunology, edited by W. E. Paul, Raven Press, Ltd., New York, see p. 926, paragraph bridging cols. 1 and 2), 1993.

Taylor et al., In vivo binding and clearance of circulating antigen by bispecific heteropolymer-mediated binding to primate erythrocyte complement receptor, J. of Immunol., vol. 148. 2462–2468, see p. 2462, second col., second full paragraph, Apr. 1992.

Kimberly et al., In Vivo Handling of Soluble Complement Fixing Ab/dsDNA Immune Complexes in Chimpanzees, J. Clin. Invest. vol. 84, 962–970, see Abstract, p. 967, first col., first full paragraph, Sep. 1989.

Emlen et al., A new ELISA for the detection of double-stranded DNA antibodies, J. Immunol. Methods, 132, 91–101, see Abstract, May 1990.

Primary Examiner—Jeffrey Stucker
Assistant Examiner—Hankyel T. Park, Ph.D
Attorney, Agent, or Firm—Oblon, Spivak, McClelland, Maier & Neustadt, P.C.

[57] ABSTRACT

Constructs consisting of antigen-based heteropolymers (AHP's) are provided. The antigen-based heteropolymers comprise at least one monoclonal antibody specific for binding to complement receptor (CR1) site on a human or non-human primate erythrocyte, and the anti-CR1 monoclonal antibody is crosslinked to an antigen specific for a target pathogenic autoantibody. Further provided is a method for treating autoimmune diseases in human or non-human primates using the AHP.

1 Claim, 9 Drawing Sheets

FIG. 9

ANTIGEN-BASED HETEROPOLYMERS AND METHOD FOR TREATING AUTOIMMUNE DISEASES USING THE SAME

This is a Division of application Ser. No. 08/202,572 filed on Feb. 28, 1994.

FIELD OF THE INVENTION

The present invention relates to antigen-based heteropolymers specific for both a specific receptor site on a primate erythrocyte and a target pathogenic autoantibody. The present invention further relates to methods for treating autoimmune diseases using these antigen-based heteropolymers.

BACKGROUND OF THE INVENTION

Circulating autoantibodies are responsible for much of the pathogenesis associated with a number of autoimmune diseases including, but not limited to, systemic lupus erythematosus (SLE), autoimmune myocarditis, immune complex mediated kidney disease, rheumatoid arthritis, myasthenia gravis, autoimmune anemias, Sjogren's Syndrome, idiopathic thrombocytopenic purpura, various forms of vasculitis, and at least some of the cellular cytotoxicity accompanying Acquired Immune Deficiency Syndrome (AIDS).

Efforts to treat autoantibody-mediated disorders have been only partially successful. Many of the past developed therapies have been based on the use of general immunosuppressive measures, through drugs or therapeutic monoclonal antibodies designed to completely abrogate antibody production. However, to date, a successful treatment has not been designed which targets the specific autoantibodies.

Plasmapheresis, which is designed to remove all the circulating antibodies, has been attempted, but only with limited success. In recent years, a variety of extracorporeal immunoabsorption procedures have been attempted. These procedures are more specific, and attempt to remove only the pathogenic autoantibodies. This involves allowing the blood or plasma to flow over matrices outside the body which contain the autoantigen which is the natural target of the autoantibodies. These methods are slow, invasive, and expensive, and are associated with several technical problems including the need to perform the procedures repeatedly because of their quantitative inefficiency. The complication of complement activation on the matrices exists. Overall, therapeutic successes have been modest, at best.

Another general, non-specific approach involves aggressive immunosuppressive therapy with corticosteroids, and cytotoxic and nonsteroidal anti-inflammatory drugs. Although in many instances clinical improvements have been obtained, there continues to be significant morbidity and mortality in autoimmune diseases despite these medications.

Therefore, notwithstanding these advances in autoimmune therapy, there remains to be seen an internal therapy which is specific for the target pathogenic autoantibody and which is both fast and quantitative.

SUMMARY OF THE INVENTION

Accordingly, it is an objective of the present invention to provide an autoimmune therapy which is highly specific for a target pathogenic autoantibody and which produces fast and quantitative results.

It is a further objective of the present invention to provide a method for treating autoimmune diseases in humans and non-human primates using such an autoimmune therapy.

The above objectives have been met by the present invention, which are called antigen-based heteropolymers. These are specific for both complement receptor site (CR1) on a primate erythrocyte and a target pathogenic autoantibody. More specifically, the above objectives have been met by the present invention which provides a complex which comprises at least one antigen-based heteropolymer comprising a monoclonal antibody specific for binding to a CR1 site on a primate erythrocyte, wherein the monoclonal antibody is crosslinked to an antigen specific for a target pathogenic autoantibody.

In addition, the objectives have been met by the present invention which further provides a method for treating autoimmune diseases by administering to a human or non-human primate an effective amount of an antigen-based heteropolymer comprised of a monoclonal antibody specific for the CR1 site on a primate erythrocyte, wherein the monoclonal antibody is crosslinked to an antigen which is specific for a target pathogenic autoantibody.

DETAILED DESCRIPTION OF THE DRAWINGS

FIG. 4 is a graph showing results of control experiments to demonstrate the specificity of binding. Human red blood cells were examined with a four-fold dilution of plasma Ma, or an IgG fraction from plasma Ma was examined. P1=plasma; N1=normal; SRBCS=sheep red blood cells; AHP=antigen-based heteropolymer; Ma=patient with severe nephritis.

FIG. 7 is a graph showing binding as a function of the concentration of IgG anti-dsDNA antibodies. A 50% dispersion of human red blood cells was examined in a mixture of bovine serum albumin and IgG Mo. The data (calculated line) was fit to a simple straight line equation by the least squares analysis.

DETAILED DESCRIPTION OF THE INVENTION

The present invention is based on the unique structural and biophysical properties of the primate red blood cell complement receptor (CR1). The antigen-based heteropolymer complexes of the present invention are specific for both the CR1 site on a primate red blood cell and for a target pathogenic autoantibody.

The antigen-based heteropolymers of the present invention are prepared from monoclonal antibodies which are specific for the CR1 receptor site on a primate erythrocyte. The monoclonal antibodies must also be capable of being crosslinked to an autoantigen which is specific for the target pathogenic autoantibody.

Examples of such monoclonal antibodies used in the present invention include 1B4, HB8592, and 7G9. HB8592 and 1B4 are disclosed in Taylor et al., "Use of heteropolymeric monoclonal antibodies to attach antigens to the C3b receptor of human erythrocytes: A potential therapeutic treatment," *Proc. Nat'l. Acad. Sci.*, 88:3305–3309 (April 1991); Reist et al., "Antigens pre-bound to the primate erythrocyte complement receptor via cross-linked bispecific monoclonal antibody heteropolymers are rapidly cleared from the circulation," *Eur. J. Immunol.*, 23:3021–3027 (1993). 7G9 is a mAb recently developed in the inventors' laboratory and can be prepared by known techniques. Other mAbs to CR1 available and useful include 3D9 and E-11 [(previously used by the present inventors in *Proc. Nat'l. Acad. Sci.*, Vol. 91 (July 1992)], and 57F and YZ1 (prepared and reported by Nussenzweig J. Exp. Med. 151:1427–1438 (1982), and Fearon J. Immunol. 134:185; (1985), respectively). It is likely that any mAb for CR1 will work successfully in the antigen-based heteropolymer system of the present invention.

The monoclonal antibody is crosslinked to an antigen specific for a target pathogenic autoantibody. The crosslinking can be performed by any efficacious crosslinking method. For example, purified monoclonal antibodies may first be biotinylated. Typically, each monoclonal antibody may contain 5 biotins. The biotinylated purified monoclonal antibody is then crosslinked to a previously biotinylated antigen or autoantigen by the use of streptavidin. Other known methods, such as use of N-succinimidyl-3-(2-pyridyldithio)propionate (SPDP) can be used for crosslinking the monoclonal antibody to the antigen if the antigen has free amino groups. The details of preparation of non-antigen-based heteropolymers can be found in Taylor et al. *Proc. Nat'l. Acad. Sci.* supra; Reist et al. supra; and Taylor et al., "In vivo binding and clearance of circulating antigen by bispecific heteropolymer-mediated binding to primate erythrocyte complement receptor," *J. Immunol.*, 148(8):2462–2468 (April 1992).

Many different autoantibodies can theoretically be cleared from the circulation of a primate by using the antigen-based heteropolymers of the present invention. Specifically, certain humans with hemophilia have been shown to be deficient in factor VIII. Recombinant factor VIII replacement treats this hemophilia. However, eventually some patients develop antibodies against factor VIII, thus interfering with the therapy. The antigen-based heteropolymer of the present invention prepared with factor VIII provides a therapeutic solution for this problem.

Specifically, an antigen-based heteropolymer comprised of factor VIII crosslinked to a mAb to CR1 specifically binds circulating anti-factor VIII autoantibodies to erythrocyte CR1 and facilitates clearance of said autoantibodies. Factor VIII is allowed to circulate and facilitate blood clotting.

Other autoantibodies which can be cleared by the antigen-based heteropolymer complex of the present invention include, but are not limited to, autoantibodies to the following antigens: the muscle acetylcholine receptor (the antibodies are associated with the disease myasthenia gravis); cardiolipin (associated with the disease lupus); platelet associated proteins (associated with the disease idiopathic thrombocytopenic purpura); the multiple antigens associated with Sjogren's Syndrome; the antigens implicated in the case of tissue transplantation autoimmune reactions; the antigens found on heart muscle (associated with the disease autoimmune myocarditis); the antigens associated with immune complex mediated kidney disease; the dsDNA and ssDNA antigens (associated with lupus nephritis); desmogleins and desmoplakins (associated with pemphigus and pemphigoid); or any other antigen which is well-characterized, can be crosslinked to an anti-CR1 mAb, and is associated with disease pathogenesis.

When the above antigen-based heteropolymer complexes are injected into the circulation of a human or non-human primate, the antigen-based heteropolymer will readily bind to the red blood cells via the monoclonal antibody at a high percentage and in agreement with the number of CR1 sites on the red blood cells. At approximately the same rate, the antigen-based heteropolymer will then bind to the autoantibody via the antigen, which is crosslinked to the monoclonal antibody. The red blood cells which contain the bound antigen-based heteropolymer autoantibody complex can then act therapeutically by facilitating the neutralization and clearance from the circulation of the bound pathogenic autoantibody. In the present invention, the antigen-based heteropolymers facilitate binding to the red blood cells and subsequently clear the autoantibody from the circulation of human and non-human primates, without also clearing the red blood cells themselves.

The present inventors have found for the first time, that by crosslinking anti-CR1 monoclonal antibodies with an autoantigen, thus generating the antigen-based heteropolymers of the present invention, it is possible to bind specifically to red blood cells the vast majority (ca. 80%–95%, Table 1 and FIG. 9) of the autoantibodies (specific for an antigen) found in plasmas from patients with a specific autoimmune disease. Specifically, the examples demonstrate that it is possible to bind specifically to red blood cells the vast majority of the autoantibodies to the dsDNA antigen found in plasmas from patients with systemic lupus erythematosus (SLE).

The present invention utilizes the unique properties of the primate red cell CR1 which enable it to bind and clear complement-opsonized immune complexes from the circulation. The immune complexes cleared via this system are taken up by the liver and spleen (Cornacoff, J. Clin. Invest. (1983)).

Figure 4:
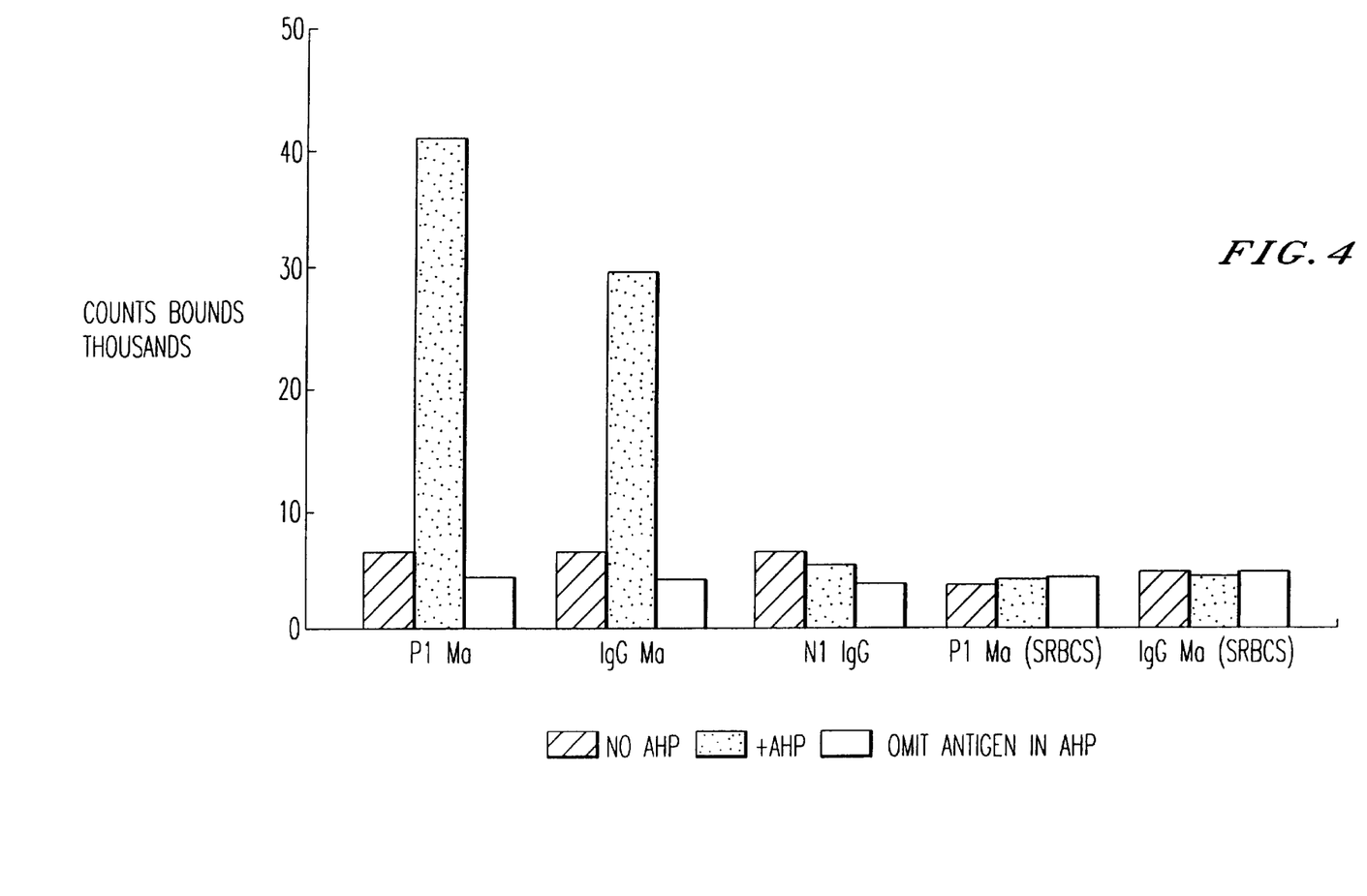
Figure 5:
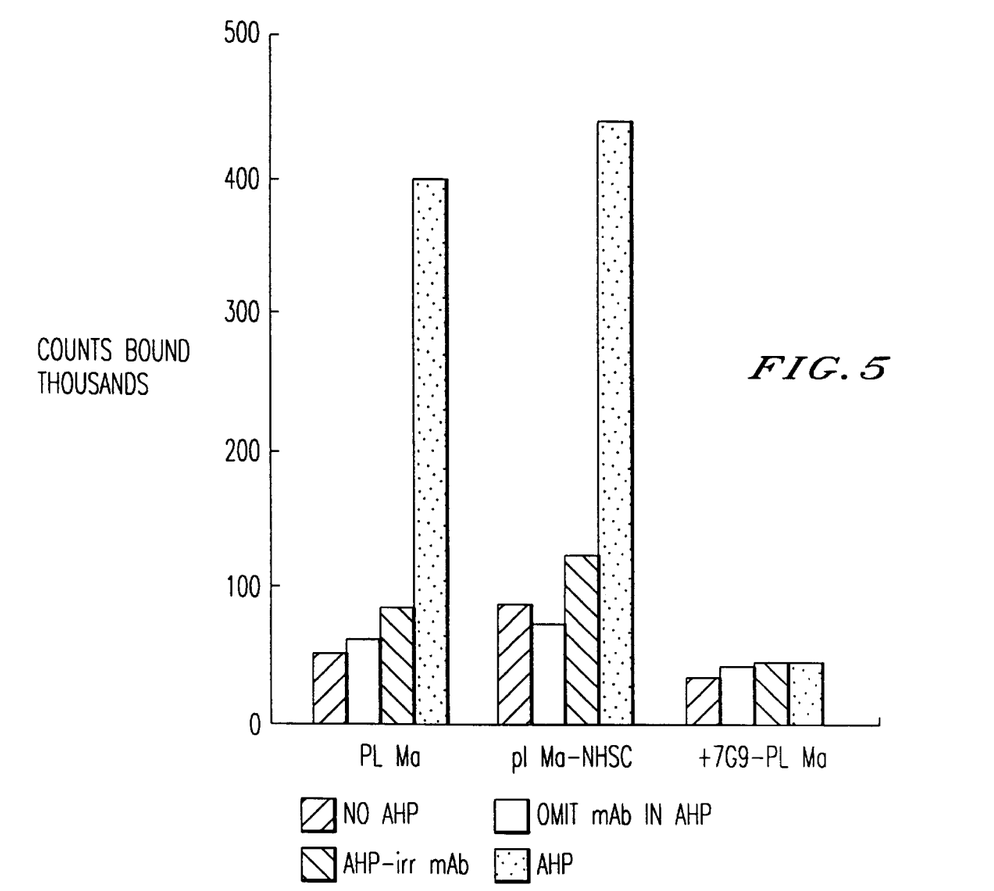
FIG. 5 is a graph showing the results of control experiments which indicate that binding is permissive in normal human serum and verify that the red blood cells are not lysed. A two-fold dilution of plasma Ma (diluted in bovine serum albumin) was compared to a similar dilution of plasma Ma in fresh, normal human serum. PL=plasma; NHSC=normal human serum complement; AHP=antigen-based heteropolymer; IRR=irrelevant monoclonal antibody.

The specificity of the binding of the AHP complex to the autoantibodies or antibodies and the red blood cell CR1-antigen-based heteropolymer complex is clear, because when a) the antigen-based heteropolymer is omitted; b) sheep red blood cells which lack the CR1 site are substituted for human red blood cells; c) the biotinylated autoantigen is omitted in preparing the antigen-based heteropolymer; and d) normal sera or normal IgG is substituted for SLE plasmas, no binding is observed (FIG. 4). Further proof of specificity is demonstrated in that no binding is observed if e) the antigen-based heteropolymer is prepared with no monoclonal antibody; f) the antigen-based heteropolymer is prepared with an "irrelevant" monoclonal antibody; and g) excess monomeric monoclonal antibody anti-CR1 is used to inhibit the antigen-based heteropolymer complex (FIG. 5). It has also been confirmed that the presence of fresh serum (as a complement source, 25% by volume) does not inhibit specific binding or lyse the red blood cells (FIG. 5).

Figure 6:
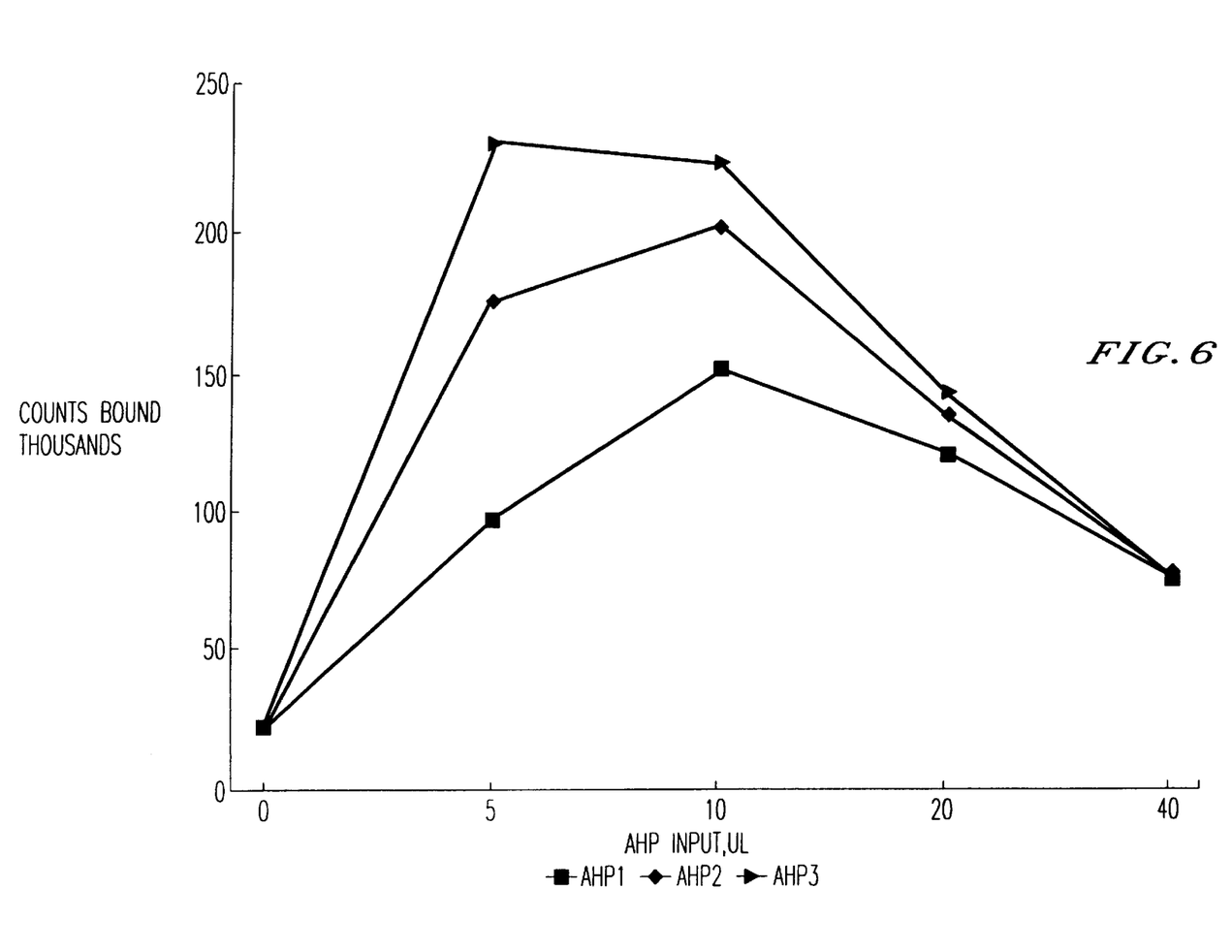
FIG. 6 is a graph showing the results of dose response experiments illustrating the optimum input of antigen-based heteropolymer to maximize binding of human IgG anti-dsDNA antibodies to 150 µl of red blood cells (50% hematocrit) in an SLE IgG sample. AHP3 was prepared as in Example 1 (see below). AHP2=contains ½ as much dsDNA as AHP3; AHP1=contains ¼ as much dsDNA as AHP3.

The input range of the antigen-based heteropolymer is determined based on the red blood cell concentration and the number of CR1 epitope sites recognized by the anti-CR1 monoclonal antibodies per red blood cell. If the antigen-based heteropolymer complex is added in excess, a fraction of the antigen-based heteropolymer will not bind to red blood cells, but will instead inhibit the uptake of the autoantibodies by the red blood cell. The reason is that when the free antigen-based heteropolymer is in solution, it will simply compete for available autoantibody with antigen-based heteropolymer bound to red blood cells. Thus, the antigen-based heteropolymer-mediated binding of the autoantibodies to human red blood cells follows a bell-shaped curve when binding is examined as a function of the input antigen-based heteropolymer concentration (FIG. 6).

The quantitative effectiveness of the antigen-based heteropolymers of the present invention in facilitating the binding of autoantibodies to red blood cells is demonstrated in the results of Farr assays.

The results of the Farr assays demonstrate that the autoantibodies are indeed specifically absorbed to red blood cells and in a high percentage (>90% in Table 1) in the presence of the antigen-based heteropolymer complex of the present invention.

Figure 7:
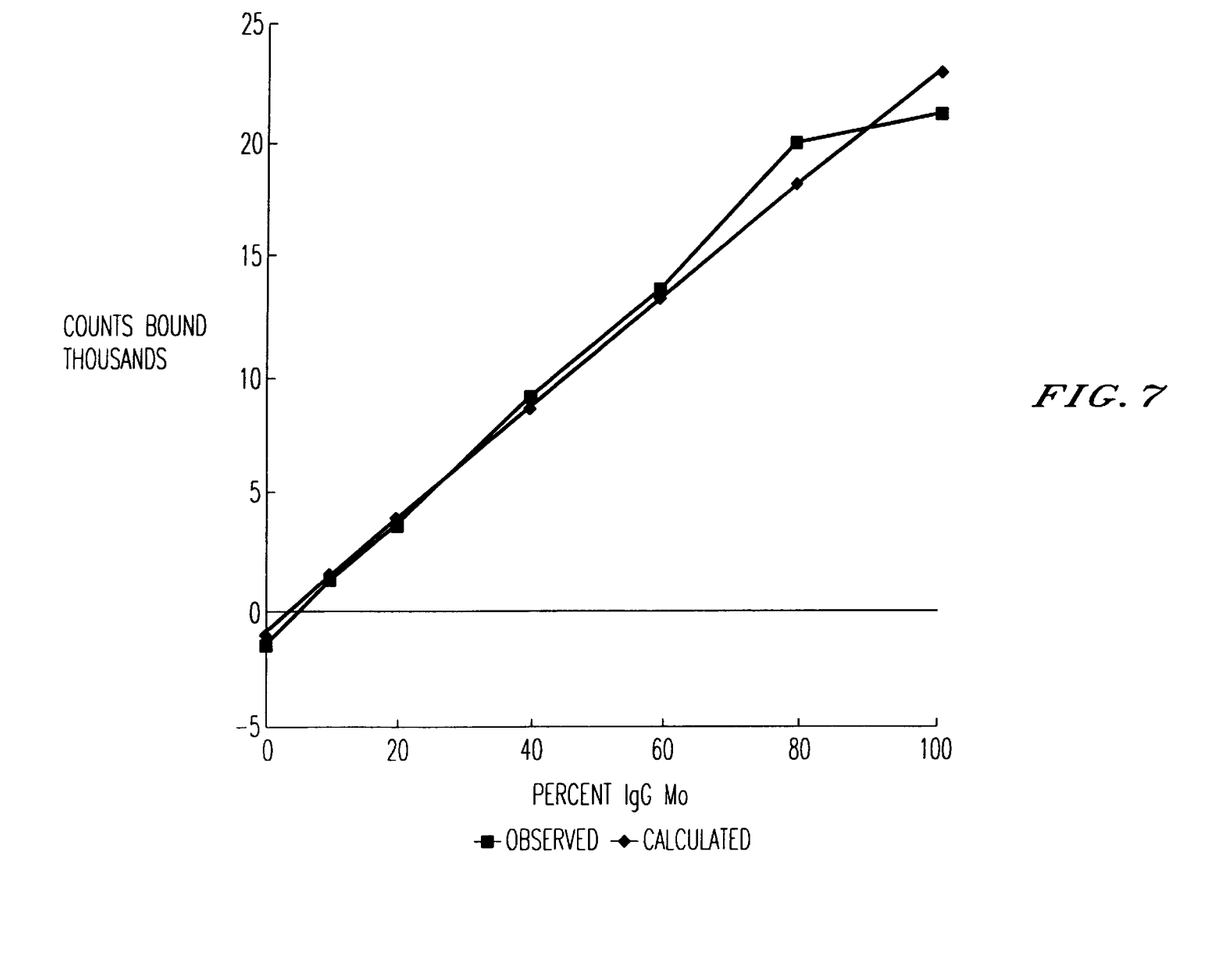
Figure 8:
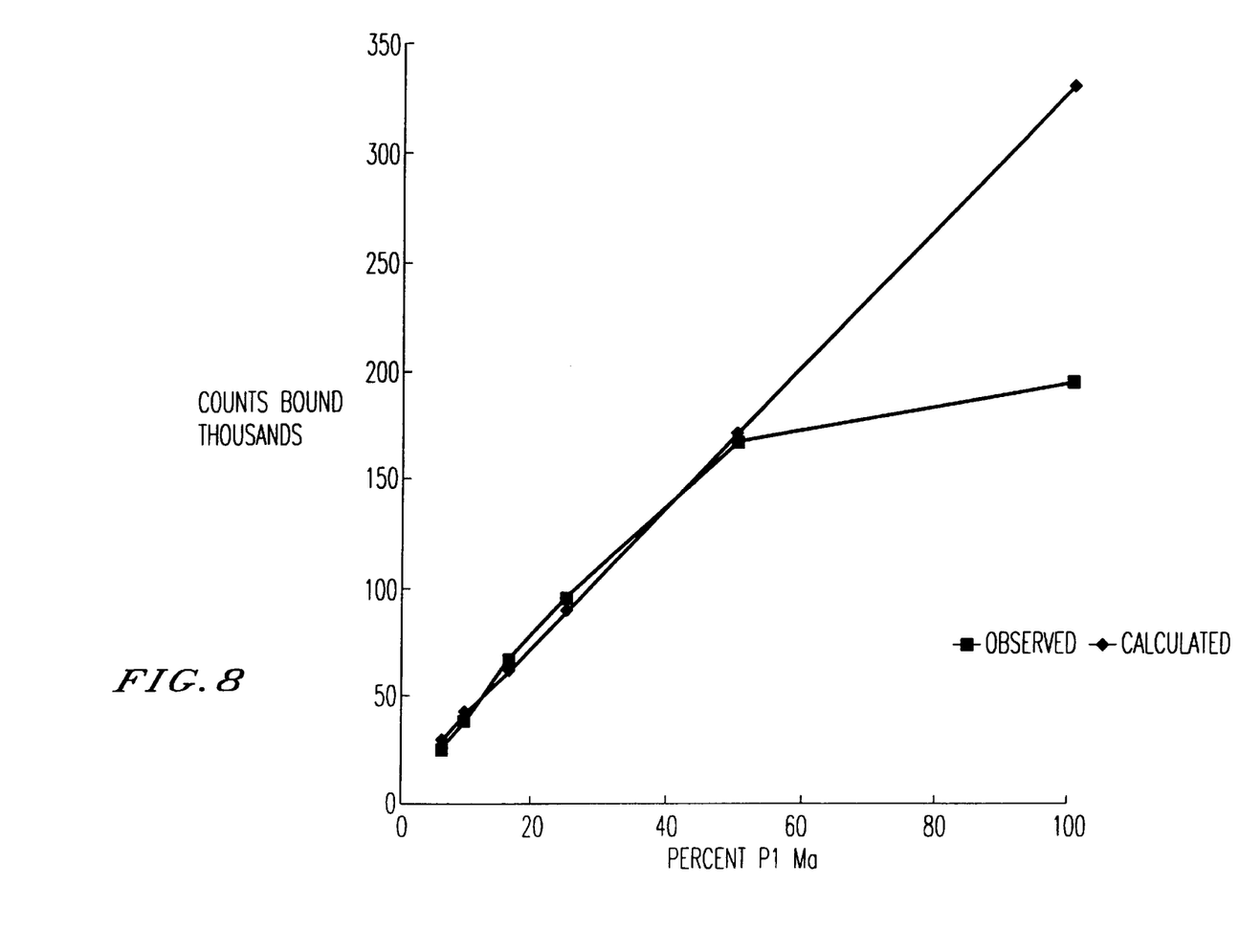
FIG. 8 is a graph showing binding as a function of the concentration of IgG anti-dsDNA antibodies using a very high titer anti-dsDNA plasma (Ma).

It has further been demonstrated that there is a linear relationship between the input of autoantibodies and the level of autoantibodies present on the red blood cells due to antigen-based heteropolymer-mediated binding (FIG. 7). In some instances the system shows a saturation because the concentration of the autoantibodies in the plasma is so high that even at the optimum input of antigen-based heteropolymers, not all of the autoantibodies can be bound to the red blood cells under standard conditions (FIG. 8). This is also shown in the Farr assays. For example, for a very high titer sera, a fraction of the autoantibody binding activity is not bound to the red blood cells (Table 1) due to its high concentration. These cases are the exception, and for the majority of samples from patients with lupus nephritis (which have pathogenic levels of anti-dsDNA antibodies), the method of the present invention removes >90% of the anti-dsDNA antibodies.

Figure 9:
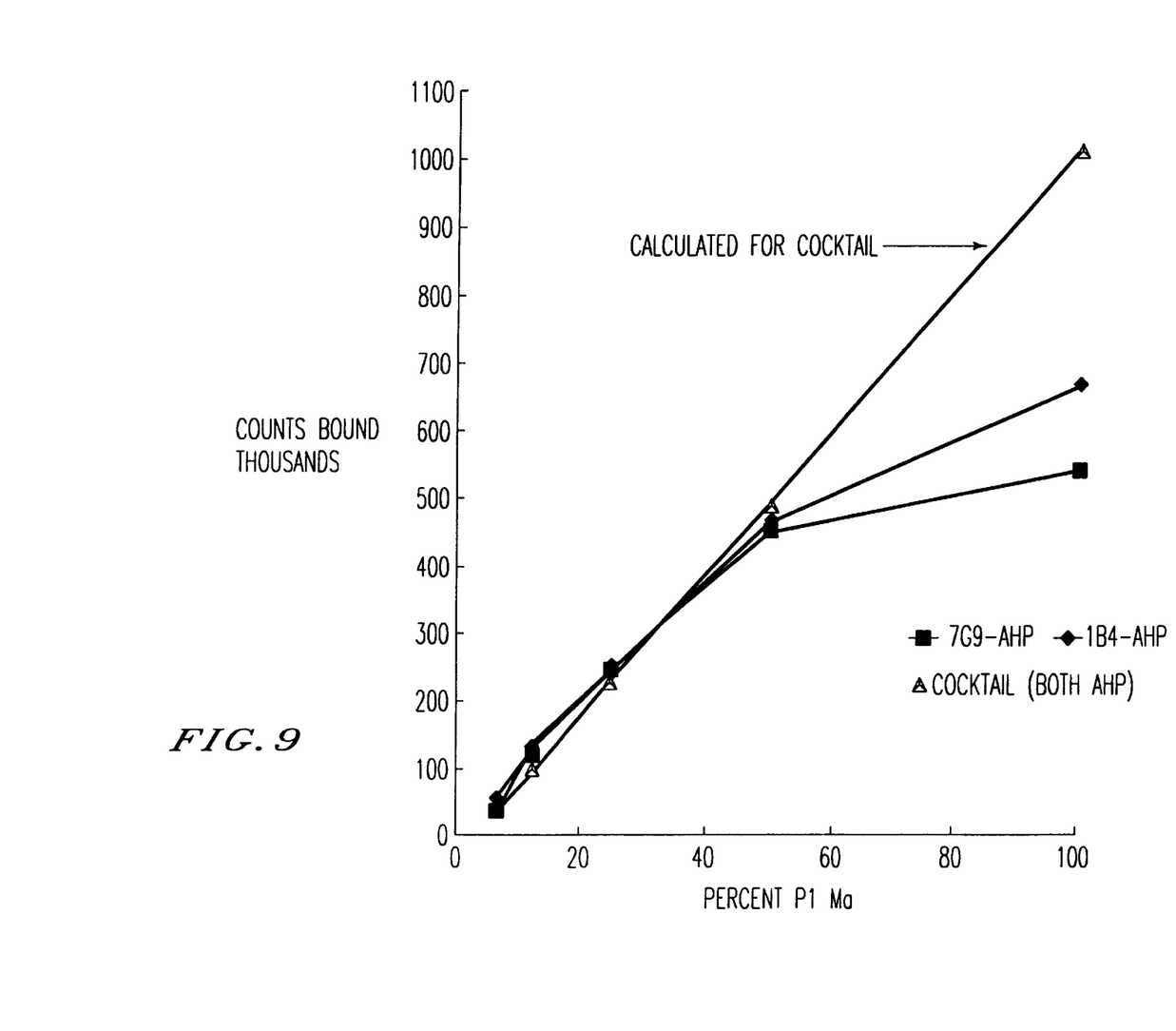
FIG. 9 is a graph showing binding as a function of the concentration of IgG anti-dsDNA antibodies using plasma Ma. (7G9 AHP and 1B4 AHP alone as compared to cocktail containing 7G9 and 1B4 together.)

However, the saturation problem can be solved by using combinations of antigen-based heteropolymer which contain monoclonal antibodies that bind to different sites on CR1. The monoclonal antibodies 7G9 and 1B4 bind to separate and non-competing sites on red blood cell CR1. Therefore, a "cocktail" containing a mixture of two antigen-based heteropolymers made with respective monoclonal antibodies gives rise to greater binding of autoantibodies to red blood cells. Plasma Ma is one of the highest titer SLE IgG anti-dsDNA plasma studied. The single antigen-based heteropolymer prepared with either anti-CR1 monoclonal antibodies 7G9 or 1B4 alone cannot absorb all anti-dsDNA antibodies to red blood cells in the undiluted plasma. However, when the "cocktail" is used, more than 90% of the IgG anti-dsDNA in plasma Ma is absorbed to red blood cells (FIG. 9). Also, the results of the Farr assay (Table 1) of the plasma supernatants indicate that greater than 90% of the anti-dsDNA antibody binding activity in plasma Ma is removed when it is treated with the antigen-based heteropolymer cocktail and red blood cells.

The present invention further encompasses a method for treating an autoimmune disease comprising administering to a primate an effective amount of an antigen-based heteropolymer complex of the present invention. The route of administration will likely be by intravenous injection into the blood of a human or non-human primate.

An effective amount of the antigen-based heteropolymer complex of the present invention is from 1–10 mg, preferably 5 mg administered once. This dosage should clear up to 2 $\mu$g/ml of the autoantibody from the circulation of a primate. In a therapeutic environment, the treatment should be repeated until complete clearance of the pathogenic autoantibody. The antigen-based heteropolymers of the present invention can be used in combination with certain fluids used for intravenous infusions.

Although the prototype studies disclosed herein are carried out using mouse mAbs, currently available technology should allow "humanization" of these mouse mAbs. This will decrease the chance that an immune response to the antigen-based heteropolymer will abrogate its effectiveness in repeated doses.

Red blood cells removed and isolated may also be used as therapeutic agents. Once franked with the antigen-based heteropolymer, these red blood cells can be reintroduced into the patient, where, in the bloodstream free autoantibodies will bind and be immobilized on the red blood cell, and subsequently cleared in accordance with the body's red blood cell clearing mechanism.

As set forth above, in an alternative embodiment, red blood cells are franked with a "cocktail" of at least two antigen-based heteropolymers, which, in addition to binding to the target autoantibody, also bind to several distinct and non-overlapping sites on CR1 of the primate red blood cell. As some of the following experiments show, by using at least two non-overlapping monoclonal antibodies for binding to CR1 on the red blood cell of primates, the number of heteropolymer complexes that can also bind is increased at a high percentage and in good agreement with the number of available binding sites. This, in turn, allows for more autoantibody binding to the heteropolymer complexes of the present invention. This augments the capability of a relatively small number of red blood cells to bind to a relatively larger amount of autoantibody, and further can facilitate the removal of the autoantibody through the normal primate immune clearance system.

The AHP of the present invention can further be used in the case of clearance of exogenous administered antibodies which become pathogenic.

EXAMPLES

Example 1
Monoclonal antibodies and crosslinked AHP anti-CR1/dsDNA complexes Three monoclonal antibodies specific for primate CR1, i.e., 1B4, HB8592, and 7G9, were purified by known methods as set forth in Reist et al., supra. The purified monoclonal antibodies were then biotinylated by known methods. Typically, each monoclonal antibody would contain 5 biotins. An amount of 24 $\mu$g of biotinylated 7G9 was incubated for 30 minutes at room temperature with 30 $\mu$g of streptavidin (SA) in a volume of 48 $\mu$l borate saline (BS buffer).

The resulting sample was then incubated with 33 $\mu$g of biotinylated dsDNA which was purchased from Dr. W. Emlen of the University of Colorado Medical Center (1 biotin per 30 base pairs in 1 ml of BS buffer) in order to crosslink 7G9 to the biotinylated dsDNA. The process was repeated using 1B4 or HB8592. The anti-CR1/dsDNA complexes formed were used without any other purification.

Example 2
Binding assays

SLE plasmas or IgG fractions from 3 different patients which are denoted by last name initials (i.e., Ma, Mo, and Ha) were incubated by general methods [Taylor et al., "The Interaction of Antibody/DNA Immune Complexes with Complement," *Arthritis and Rheumatism*, 30(2):176–185 (February 1987)] with red blood cells and AHP (10 $\mu$l AHP3 per 150 $\mu$l of 50% red cells) (solid symbols in FIG. 2) and without AHP (open symbols in FIG. 2) for the indicated time period at 37° C. as follows: Type O red blood cells were washed and then reconstituted to a 50% hematocrit in one of the above plasmas. The AHP was added in an "equivalence" of ca. 0.6–1.2 $\mu$g of anti-CR1 mAb per ml blood based on 500–1000 CR1 receptors per red blood cell. After brief incubation, the sample was centrifuged and the supernatant isolated and saved for an independent assay (Farr assay) of the anti-dsDNA antibodies. The red cell pellets were washed 3 times and then an $^{125}$I-labeled monoclonal antibody to human IgG (HB43) was added to the red blood cells to measure uptake of human IgG. (Taylor et al., 88:3305–3309, *Proc. Natl. Acad. Sci.* supra.) The arrow at the bottom of FIG. 2 emphasizes the low level of background binding to red blood cells of all 3 samples after a full 15 minute incubation. The broken lines at the bottom left of the figure are extrapolations to 0 minutes of incubation with the AHP.

Figure 1:
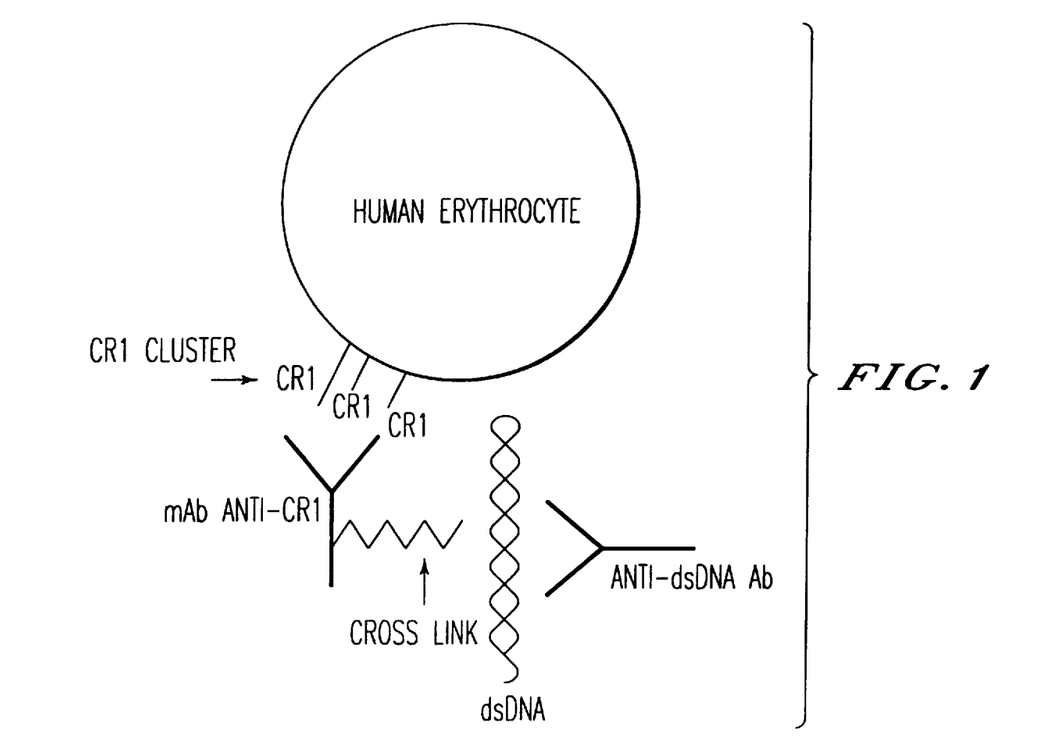
FIG. 1 is a schematic illustration of the antigen-based heteropolymer complex consisting of a monoclonal antibody bound to the CR1 receptor site on a primate erythrocyte. The monoclonal antibody is also crosslinked to an autoantigen (dsDNA) which in turn, is bound to the target pathogenic autoantibody (anti-dsDNA antibody).
Figure 2:
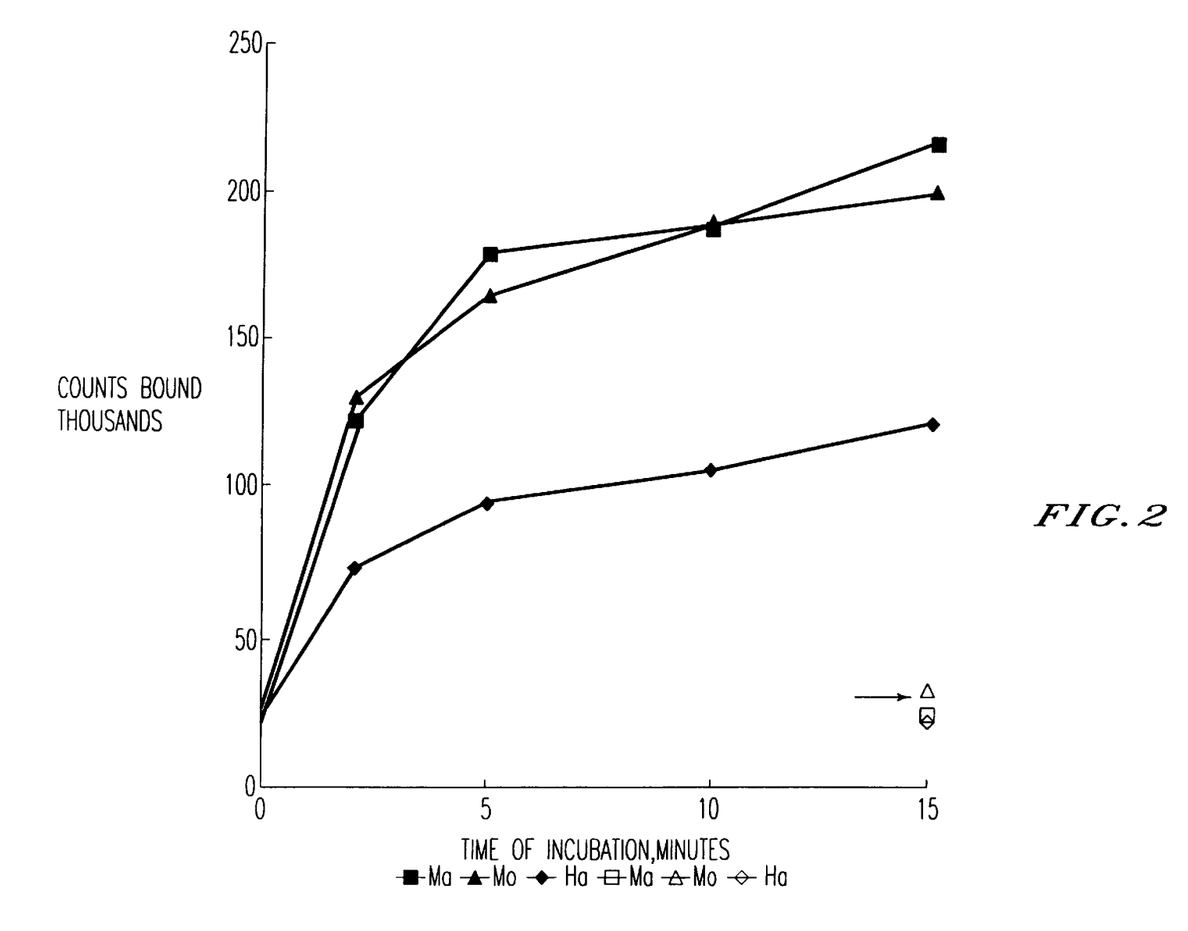
FIG. 2 is a graph showing the kinetics of the antigen-based heteropolymer-mediated binding of IgG anti-dsDNA antibodies to human red blood cells. The counts bound are proportional to the amount of human IgG bound (see below). Ma, Mo, and Ha are the last name initials of SLE patients from whom the plasmas or IgG fractions were taken. The solid symbols indicate incubation with red blood cells and antigen-based heteropolymer, and the above respective antibodies. The open symbols represent incubation with red blood cells and antibodies, without antigen-based heteropolymer.

FIG. 2 demonstrates the results of the kinetics of AHP-mediated binding of IgG anti-dsDNA antibodies to human red blood cells. These results show that the complexes of the present invention bind to red blood cells. The results further show that by virtue of the incorporated dsDNA, the AHP complexes facilitate the specific and rapid binding (ca. 80% complete in ca. 5 minutes at 37° C. as shown in FIG. 2) to red blood cells of high avidity IgG and/or IgM/anti-dsDNA antibodies found in SLE plasmas. The specificity of the binding for anti-dsDNA antibodies and the anti-CR1/dsDNA AHP complex is clear due to the fact that all the binding is abrogated when the AHP is omitted (open symbols in FIG. 2).

Example 3
Two SLE samples were prepared as in Example 2 above. However, the samples were incubated with AHP for 15 minutes at 37° C.

Figure 3:
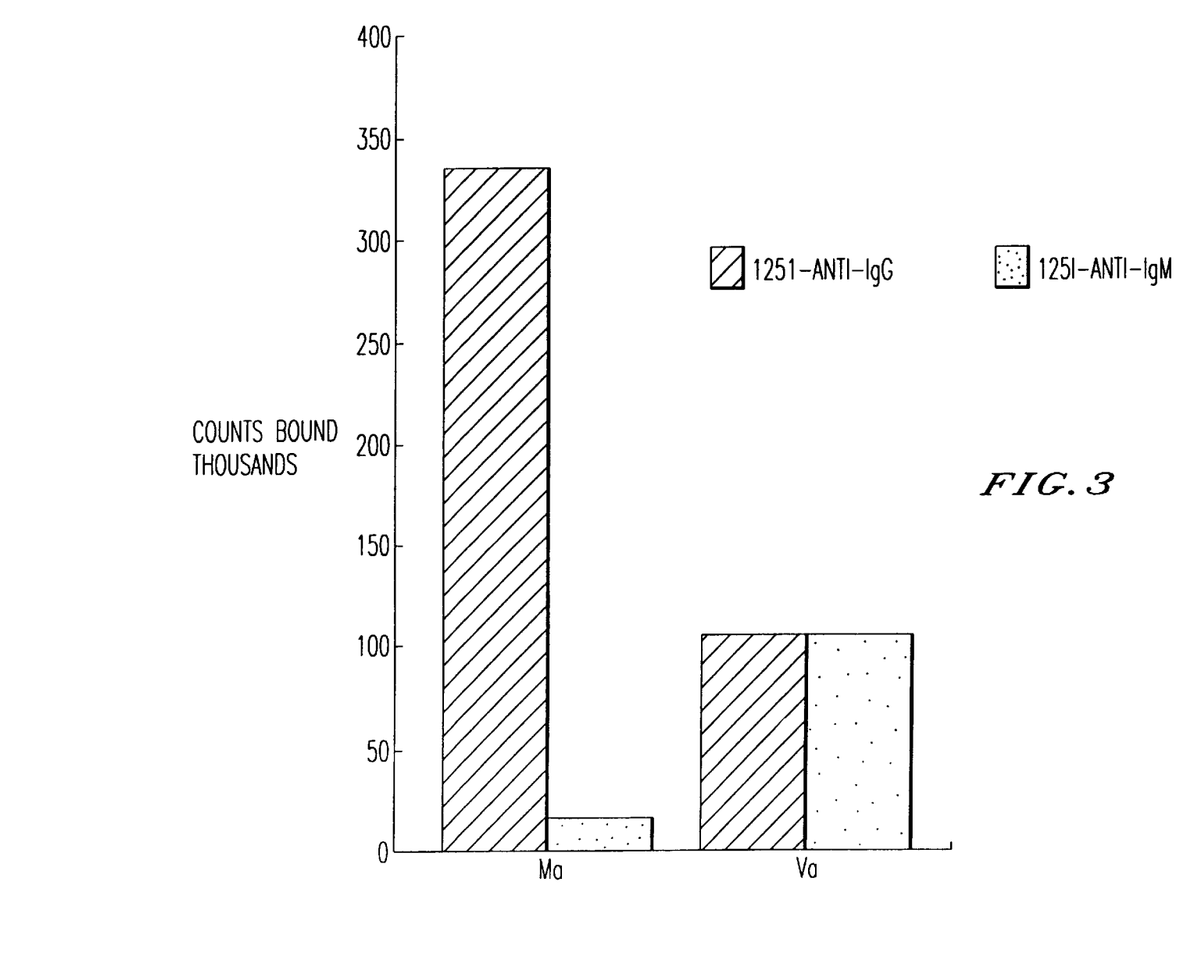
FIG. 3 is a graph showing examination of red blood cells prepared and incubated as described in FIG. 2, and probed with $^{125}$I-labeled monoclonal antibodies to both human IgG and human IgM. Plasma Ma is representative of samples from patients with severe nephritis and contains almost exclusively IgG anti-dsDNA antibodies at a very high titer. Plasma Va contains both IgG and IgM anti-dsDNA antibodies.

Plasma Ma, as shown in FIG. 3, is representative of samples from patients with severe nephritis, and as previously reported, has almost exclusively IgG anti-dsDNA antibodies at very high titer [Taylor et al., *Arthritis and Rheumatism*, (1987)]. The plasma Va was shown in Taylor et al. to have both IgG and IgM anti-dsDNA antibodies.

The red blood cells were probed with $^{125}$I-labeled monoclonal antibodies to both human IgG (HB43) and human IgM (HB57).

Example 4
Control experiments to demonstrate the specificity of binding

Plasma Ma, or an IgG fraction from plasma Ma, was prepared as set forth above. The plasma Ma and the IgG fraction from plasma Ma were diluted four-fold. Human red blood cells were used as above in this experiment. Five different samples were prepared as follows: a) AHP omitted; b) sheep red blood cells (SRBCS) lacking the CR1 site were substituted for human red blood cells; c) the biotinylated dsDNA was omitted in preparing the AHP; and d) normal plasma or normal IgG was substituted for SLE plasma (FIG. 4).

The results shown in FIG. 4 demonstrate that only in the presence of the AHP and human red blood cells (first 2 groups of FIG. 4 on the left) is binding evident. If AHP is omitted or the dsDNA antigen is omitted from the AHP, no binding is seen. Further, when sheep red blood cells were used with Ma, or normal human IgG was used in place of Ma, binding was also reduced to background levels.

Example 5
In this experiment, a two-fold dilution of plasma Ma (diluted in bovine serum albumin) was compared to the same dilution of plasma Ma in fresh normal human serum. The following four samples were prepared: a) the AHP was prepared with no monoclonal antibody; b) the AHP was prepared with a monoclonal antibody to the dinitrophenol group (23D1, an irrelevant (IRR) antibody); c) excess monomeric 7G9 anti-CR1 was used to inhibit the 7G9/dsDNA AHP; and d) serum prepared with AHP.

The proof of specificity is demonstrated in FIG. 5 by the showing that no binding is observed if the AHP is prepared with no monoclonal antibody, the AHP is prepared with an irrelevant monoclonal antibody, or if excess monomeric 7G9 anti-CR1 is used to inhibit the 7G9/dsDNA AHP. The specificity of the AHP, which contains biotinylated monoclonal antibody 7G9, is demonstrated because excess monoclonal antibody 7G9 is able to compete for sites on CR1 and abrogate all binding. It has also been confirmed that the presence of fresh serum (as a complement source, 25% by volume) does not inhibit specific binding or lyse the red blood cells (FIG. 5).

Example 6
Farr assay showing quantitative effectiveness of the antigen-based heteropolymers The quantitative effectiveness of the antigen-based heteropolymer complexes of the present invention in facilitating binding of target autoantibodies to red blood cells is demonstrated in Table 1 which shows the results of Farr assays. The Farr assay was performed as in Taylor et al., *Arthritis and Rheumatism*, supra. These assays are specific for anti-dsDNA antibodies. The supernatant samples contain the plasma proteins and the vast majority of IgG, not specific for dsDNA, which did not bind to red blood cells. These assays indicate that the anti-dsDNA binding activity in the supernatants is reduced considerably for most SLE plasma and IgG fractions (more than 90% in Table 1). That is, the IgG anti-dsDNA antibodies are indeed specifically absorbed to the red blood cells in the presence of the AHP complex.

TABLE 1

Efficiency of Removal of Anti-dsDNA Antibody Binding Activity from SLE Plasmas by adsorption to Red Cells in the Presence of a Specific AHP. Analysis of binding of $^3$H-dsDNA in the Farr Assay. $^3$H-dsDNA (DPM) in the SN (Unbound Counts)

| SLE Plasma[a] | Dilution[b] tested in Farr assay | Adsorbed with red cells alone | Adsorbed with red cells +AHP | % Adsorbed[c] |
|---|---|---|---|---|
| Ma/2 | 5 | 58 | 710 | 95 |
|  | 25 | 270 | 950 |  |
|  | 100 | 700 | 970 |  |
|  |  | NL IgG[d]: |  |  |
|  |  | (1000) |  |  |
| Va/1 | 10 | 680 | 1400 | 90 |
|  | 25 | 1040 |  |  |
|  | 100 | 1420 |  |  |
|  |  | NL IgG[d]: |  |  |
|  |  | (1800) |  |  |
| Co/1 | 4 | 730 | 1250 | 80 |
|  | 20 | 1280 | 1830 |  |
|  | 40 | 1550 | 2300 |  |
|  |  | NL IgG[d]: |  |  |
|  |  | (2600) |  |  |
| Ha/2 | 5 | 30 | 120 | 85, 95 |
|  | 20 | 90 | 360 |  |
|  | 80 | 270 | 630 |  |
|  | 320 | 390 | 680 |  |
|  |  | NL IgG[d]: |  |  |
|  |  | (1200) |  |  |
| Ma/1 | 4 | 370 | 1760 | 90[e] |
|  | 8 | 470 |  |  |
|  | 16 | 970 |  |  |
|  | 32 | 1700 |  |  |
|  |  | NL IgG[d]: |  |  |
|  |  | (3000) |  |  |

[a]Dilution of SLE plasma incubated with the red cells (±AHP).
[b]Dilutions of material not bound to red cells tested in Farr assay.
[c]Percent adsorbed calculated based on relative dilution of "+AHP" sample needed to give same level of binding as sample lacking AHP. Unless otherwise specified, 7G9 was used to generate the AHP.
[d]In Farr assays, IgG antibodies are precipitated with saturated ammonium sulfate, and then dsDNA not bound to the anti-dsDNA antibodies is measured in the supernatant (SN). The background binding level for normal IgG is given for each assay. A number of dsDNA preparations of different input and specific activity were tested.
[e]A "cocktail" of the AHP prepared with both 7G9 and 1B4 was tested. When the two AHP's were each evaluated separately, only 70% of the anti-dsDNA binding activity was adsorbed.

The above results demonstrate that the autoantibodies are indeed specifically absorbed to red blood cells and in a high percentage (>90%) in the presence of the antigen-based heteropolymer complex of the present invention.

Example 7

Dose response experiments

AHP1, AHP2 and AHP3 were prepared as follows. AHP3 was prepared in accordance with the procedures set forth in Example 1 using 10 μl of AHP3 per 150 μl of 50% red blood cells. AHP1 and AHP2 were prepared accordingly, except that AHP2 contains ½ as much dsDNA as AHP3, and AHP1 contains ¼ as much dsDNA as AHP3.

Dose response experiments were performed to find the optimum input of AHP to maximize binding of human IgG anti-dsDNA antibodies to 150 μl of human red blood cells (50% hematocrit) in an SLE IgG sample.

The AHP-mediated binding of IgG anti-dsDNA antibodies to human red blood cells follows a bell-shaped curve when binding is examined as a function of the input AHP concentration (FIG. 6).

AHP3 was chosen as the exemplified AHP because it facilitates the highest level of binding IgG anti-dsDNA to red blood cells.

This data shows that the input range of AHP is determined based on the red blood cell concentration and the number of CR1 epitope sites (recognized by the anti-CR1 monoclonal antibodies) per red blood cell. It is clear that if the AHP is added in excess, a fraction of the AHP will not bind to the red blood cells and will instead, inhibit uptake of the autoantibodies by the red blood cell. The reason is that the free AHP in solution will simply compete for available autoantibody with AHP bound to red blood cells.

Example 8

Dose response experiment as a function of autoantibody concentration

A 50% dispersion of human red blood cells was examined in mixtures of bovine serum albumin and IgG Mo. FIG. 7 shows the results of this binding experiment. The results indicate that there is a linear relationship between counts bound (level of bound IgG) and the input level of SLE IgG anti-dsDNA antibodies due to AHP-mediated binding. The data was calculated to fit a simple straight line equation by least squares analysis.

Example 9

A similar experiment as in experiment 8 was performed except, in this case, a very high titer anti-dsDNA plasma (Ma) was examined. When the sample was used and diluted, it was clear that not all the endogenous IgG anti-dsDNA is bound by the red blood cells. Therefore, in some instances, the system shows saturation because the concentration of IgG anti-dsDNA antibodies in the SLE plasma is so high that even at optimum input of AHP, not all the IgG anti-dsDNA antibodies can be bound to the red blood cells under standard conditions (FIG. 8). This is also shown in the Farr assays (below) where it has been found that for very high titer plasma, a substantial fraction of the anti-dsDNA antibody binding activity is not bound to the red blood cells (see Table 1). Fortunately, these cases are the exceptions. For the majority of SLE plasma from patients with lupus nephritis (and pathogenic levels of anti-dsDNA antibodies) which were examined, the method does remove greater than 90% of the anti-dsDNA antibodies.

Example 10

Binding as a function of the concentration of IgG anti-dsDNA antibodies using AHP "cocktail"

Combinations of AHP were prepared which contain monoclonal antibodies that bind to different sites on CR1. The monoclonal antibodies 7G9 and 1B4 bind to separate and non-competing sites on the CR1 site of the red blood cell. These "cocktails" produced contain a mixture of the two AHP's made with these respective monoclonal antibodies. The results as shown in FIG. 9 show that use of a "cocktail" gives rise to even greater binding of IgG anti-dsDNA antibodies to red blood cells.

As set forth above, plasma Ma is one of the highest titer SLE IgG anti-dsDNA plasma which has been studied. The single AHP prepared with either anti-CR1 monoclonal antibody 7G9 or 1B4 alone cannot absorb all the anti-dsDNA antibodies to red blood cells in the undiluted plasma. However, when the "cocktail" is used, the continued linearity in the binding (even in the undiluted plasma) suggests that it is possible to absorb to red blood cells, more than 90% of the IgG anti-dsDNA in plasma Ma (FIG. 9). This was confirmed in the Farr assays (see Table 1) of the plasma supernatants which indicated that greater than 90% of the anti-dsDNA antibody binding activity in plasma Ma is removed when it is treated with the AHP "cocktail" and human red blood cells.

The AHP prepared with anti-CR1 monoclonal antibody 1B4 showed slightly better binding than the AHP prepared with monoclonal antibody 7G9. However, saturation at the highest input of Ma was seen in both cases. When the "cocktail" containing both AHP's was used, on the other hand, binding was enhanced considerably which suggests that all the IgG anti-dsDNA can be bound to red blood cells (FIG. 9).

What is claimed is:

1. An antigen-based heteropolymer (AHP) cocktail, comprising at least two AHP's wherein each said AHP comprises a monoclonal antibody specific for binding to complement receptor (CR1) site on a primate erythrocyte, and wherein said monoclonal antibody is crosslinked to an antigen specific for either a target pathogenic antibody or an autoantibody.

* * * * *

UNITED STATES PATENT AND TRADEMARK OFFICE
CERTIFICATE OF CORRECTION

PATENT NO. : 5,879,679
DATED : March 9, 1999
INVENTOR(S) : Ronald P. Taylor, et al.

It is certified that error appears in the above-identified patent and that said Letters Patent is hereby corrected as shown below:

Column 1,
Line 7, the following paragraph is inserted:
-- U.S. Government Rights This invention was made with United States Government support under Grant No. AR43307, awarded by the National Institutes of Health. The United States Government has certain rights in the invention. --

Signed and Sealed this

Thirtieth Day of October, 2001

Attest:

*Nicholas P. Godici*

NICHOLAS P. GODICI
*Attesting Officer*     *Acting Director of the United States Patent and Trademark Office*